(12) United States Patent
Meine et al.

(10) Patent No.: US 10,329,517 B2
(45) Date of Patent: Jun. 25, 2019

(54) ACID LIQUID COMPACT WASHING AGENT INCLUDING HYDROXYCARBOXYLIC ACID, NON-IONIC SURFACTANT, AND AN-AMYLASE

(71) Applicant: Henkel AG & Co. KGaA, Duesseldorf (DE)

(72) Inventors: Georg Meine, Mettmann (DE); Timothy O'Connell, Landsberg am Lech (DE)

(73) Assignee: Henkel AG & Co. KGaA (DE)

( * ) Notice: Subject to any disclaimer, the term of this patent is extended or adjusted under 35 U.S.C. 154(b) by 0 days.

(21) Appl. No.: 15/662,426

(22) Filed: Jul. 28, 2017

(65) Prior Publication Data

US 2017/0321151 A1    Nov. 9, 2017

Related U.S. Application Data

(63) Continuation of application No. PCT/EP2015/075795, filed on Nov. 5, 2015.

(30) Foreign Application Priority Data

Jan. 30, 2015  (DE) .................. 10 2015 201 698

(51) Int. Cl.
| | |
|---|---|
| C11D 1/72 | (2006.01) |
| C11D 1/04 | (2006.01) |
| C11D 1/66 | (2006.01) |
| C11D 3/20 | (2006.01) |
| C11D 3/386 | (2006.01) |
| C11D 17/04 | (2006.01) |
| C11D 1/83 | (2006.01) |
| A61K 8/365 | (2006.01) |
| C07C 55/02 | (2006.01) |

(52) U.S. Cl.
CPC .................. *C11D 1/04* (2013.01); *C11D 1/66* (2013.01); *C11D 3/2086* (2013.01); *C11D 3/38618* (2013.01); *C11D 17/043* (2013.01); *A61K 8/365* (2013.01); *C07C 55/02* (2013.01); *C11D 1/72* (2013.01); *C11D 1/83* (2013.01); *C12Y 302/01001* (2013.01)

(58) Field of Classification Search
CPC ...... C11D 1/72; C11D 3/2086; C11D 3/38618
See application file for complete search history.

(56) References Cited

U.S. PATENT DOCUMENTS

| | | | |
|---|---|---|---|
| 3,547,828 A | 12/1970 | Mansfield et al. | |
| 3,839,318 A | 10/1974 | Mansfield | |
| 5,374,716 A | 12/1994 | Biermann et al. | |
| 5,441,662 A * | 8/1995 | Schwadtke | C11D 3/2065 |
| | | | 510/321 |

FOREIGN PATENT DOCUMENTS

| | | |
|---|---|---|
| DE | 10027975 A1 | 12/2001 |
| DE | 10031014 A1 | 1/2002 |
| DE | 10138094 A1 | 2/2003 |
| EP | 0186242 A1 | 7/1986 |
| WO | 9115192 A1 | 10/1991 |
| WO | 9219711 A1 | 11/1992 |
| WO | 9310208 A1 | 5/1993 |
| WO | 9426857 A1 | 11/1994 |
| WO | 9950380 A1 | 10/1999 |
| WO | WO 99/50380 * | 10/1999 |
| WO | 03013450 A2 | 2/2003 |
| WO | 2014162001 A1 | 10/2014 |

OTHER PUBLICATIONS

PCT International Search Report, PCT/EP2015/075795, Completed: Jan. 14, 2016; dated Feb. 15, 2016, 4 pages.
Fischer, Karl Dr. "Neues Verfahren zur massanalytischen Bestimmung des Wassergehaltes von Fluessigkeiten und festen Koerpern." Angewandte Chemie, vol. 48, No. 26, May 31, 1935, pp. 394-396. ISBN 3-540-12846-8.
Griffin, William C. "Classification of Surface-Active Agents by 'HLB'." Journal of the Society of Cosmetic Chemists, vol. 1, 1949, pp. 311-326.
Tsujita, Yoshio, et al. "Presence and Partial Characterization of Internal Acid Protease of Aspergillus oryzae." Applied and Environmental Microbiology, vol. 36, No. 2, Aug. 1978, pp. 237-242.
Chang, Chen-Tien et al. "Purification and Properties of Alpha-Amylase from Aspergillus oryzae ATCC 76080." Biochemistry and Molecular Biology International, vol. 36, No. 1, May 1995, pp. 185-193. XP002752692.
Samie, Nima, et al. "Novel extracellular hyper acidophil and thermostable alpha-amylase from *Micrococcus* sp.NS 211." Starch Journal, vol. 64, Nov. 7, 2011, pp. 136-144. DOI: 10.1002/star.201100108. XP002752693.
Asoodeh, Ahmad, et al. "A novel thermostable, acidophilic alpha-amylase from a new thermophilic "*Bacillus* sp. Ferdowsicous" isolated from Ferdows hot mineral spring in Iran: Purification and biochemical characterization." International Journal of Biological Macromolecules, vol. 46, No. 3, Apr. 2010, pp. 289-297. XP002752694.
Rodriguez, J. et al. "Purification and properties of a chitinase from Pencillium oxalicum autolysates." Letters in Applied Microbiology, vol. 20 No. 1, Jan. 1995. pp. 46-49. XP0027525695.
Seung, Ho Lee, et al. "Characterization, Gene Cloning, and Sequencing of a Fungal Phytase, PhyA, from Pencillium oxalicum PJ3." Preparative Biochemistry and Biotechnology, vol. 45, No. 4, May 19, 2014, pp. 336-347. DOI: 10.1080/10826068.2014.923446. XP002752696.

(Continued)

*Primary Examiner* — Brian P Mruk
(74) *Attorney, Agent, or Firm* — Thomas G. Krivulka

(57) ABSTRACT

The invention relates to liquid washing agents having a pH value of <6.5, preferably in the range of 2 to 5, containing, based on the total weight of the liquid washing agent, (i) 5 to 30% by weight, preferably 10 to 30% by weight, in particular 15 to 25% by weight of at least one hydroxycarboxylic acid having 2 to 8 carbon atoms, (ii) 15 to 55% by weight, preferably 20 to 55% by weight, in particular 35 to 50% by weight of at least one non-ionic surfactant, (iii) 0 to 20% by weight of water, and (iv) at least one α-amylase having a pH optimum of pH <7. Said liquid washing agents have an increased cleaning power, in particular on stains on the basis of components and residues from deodorants but also of grates, berries, tea and red wine residues.

10 Claims, No Drawings

(56) References Cited

OTHER PUBLICATIONS

Kurakake Masahiro, et al. "Production of Galacto-manno-oligosaccharides from Guar Gum by Beta-Mannanase from Pencillium oxalicum SO." Journal of Agricultural and Food Chemistry, vol. 54, No. 20, 2006, pp. 7885-7889. XP002752697.

Novozymes A/C, et al. "Enzymer til uddannelsesinstitutioner." Nov. 2014. XP002752699. http://web.archive.org/web/20141101182716/http://www.easj.dk/enzymer/.

"Termamyl". Enzyme Information. https://bioenv.gu.se/digitalAssets/1608/1608318_enzyme-information.pdf.

Shandong Longda Bio-Products Co., Ltd. Ldzymes. "Fungal alpha amylase". http://www.enzymeinchina.com/4-fungal-alpha-amylase.html.

\* cited by examiner

ACID LIQUID COMPACT WASHING AGENT INCLUDING HYDROXYCARBOXYLIC ACID, NON-IONIC SURFACTANT, AND AN-AMYLASE

FIELD OF THE INVENTION

The present invention generally relates to anhydrous to low-water liquid washing agent compositions having acid pH value, which contain at least one low-molecular-weight hydroxycarboxylic acid, at least one non-ionic surfactant, and at least one α-amylase having a pH optimum of pH <7, the use of such liquid washing agents for removing stains, in particular on the basis of components and residues of deodorants, but also of rust, berries, tea, and red wine, and to a washing method in which such an agent is used.

BACKGROUND OF THE INVENTION

Deodorants which are used by consumers form poorly-soluble, yellow residues on worn textiles with secretions of the human skin, these residues substantially containing aluminum hydroxychloride, perfumed oil components, waxes, for example, myristyl myristate, and human components of the skin and low-molecular-weight fatty acids of sweat. Further poorly-soluble stains on textiles can originate from rust and food residues, in particular berries, tea, and red wine.

Conventional liquid washing agents are based on surfactant mixtures which comprise, for example, soaps, fatty alcohol ether sulfates, and fatty alcohol ethoxylates, wherein the total surfactant quantities in liquid washing agents are approximately 20 wt. % and in concentrated agents are approximately 50 wt. %. However, such known liquid washing agents remove such poorly soluble residues not at all or only inadequately. It is therefore a general aspiration to provide liquid washing agents having improved cleaning power, in particular on stains which are based on components and residues of deodorants, but also on rust, berries, tea, and red wine. In this case, the cleaning power of the washing agents on enzyme-sensitive stains is also to be provided.

BRIEF SUMMARY OF THE INVENTION

In a first aspect, the present invention therefore relates to a liquid washing agent which, in relation to the total weight of the liquid washing agent, contains:
(i) 5 to 30 wt. %, preferably 10 to 30 wt. %, in particular 15 to 25 wt. % of at least one hydroxycarboxylic acid having 2 to 8 carbon atoms and
(ii) 15 to 55 wt. %, preferably 20 to 55 wt. %, in particular 35 to 50 wt. % of at least one non-ionic surfactant,
(iii) 0 to 20 wt. % water,
(iv) at least one α-amylase having a pH optimum of pH <7
(v) wherein the liquid washing agent has a pH value <6.5, preferably in the range of 2 to 5.

In a further aspect, the present invention is directed to the use of the liquid washing agent described herein for washing textiles, in particular for removing stains which are based on components and residues of deodorants, rust, berries, tea, and red wine.

Finally, in a further aspect, the present invention relates to a washing method for washing textiles, wherein the low-water to anhydrous liquid washing agent as described herein is used.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

It has surprisingly been found that in liquid washing agents which are low-water to anhydrous, contain 5 to 30 wt. %, preferably 10 to 30 wt. %, in particular 15 to 25 wt. % low molecular weight hydroxycarboxylic acid and 5 to 55 wt. %, preferably 20 to 55 wt. %, in particular 35 to 50 wt. % of at least one non-ionic surfactant, and have a pH value <6.5, preferably in the range of 2 to 5, particularly preferably a pH of 4.6, α-amylases having a pH optimum of pH <7 may be incorporated more stably and these washing agents have an increased cleaning power, in particular on stains which are based on components and residues of deodorants, but also on rust, berries, tea, and red wine residues.

Cleaning power (washing power) is understood in the scope of the invention as the removal of one or more stains, in particular laundry stains, which are bleach-sensitive, enzyme-sensitive, or surfactant-sensitive, in particular surfactant-sensitive. The removal can both be detected metrologically and also judged visually via lightening of the stain.

The washing agents described herein can be washing agents for textiles or natural fibers. The washing agents in the scope of the invention furthermore include washing aids, which are added to the actual washing agent during the manual or machine textile laundry, to achieve a further effect or to amplify an effect. Furthermore, washing agents in the scope of the invention also include textile pretreatment and posttreatment agents, i.e., those agents with which the item of laundry is brought into contact before the actual laundry, for example, to dissolve difficult stains, and also those agents which, in a step following the actual textile laundry, provide the washed material with further desirable properties such as a pleasant feeling, freedom from wrinkles, or low static charge. The last agents include, inter alia, fabric softeners.

By way of the use of the liquid washing agent described herein, stains which are based on components and residues of deodorants, but also stains with rust, berries, tea, and red wine may be removed. The spot removal is significantly improved by a pretreatment of the relevant textile at the soiled point. A certain moisture of the textiles strengthens the effect of the citric acid. In spite of the low pH value, the α-amylase according to the invention may be incorporated stably into said washing agent.

In particular, low-water compositions according to the invention preferably contain 5 to 20 wt. % water, more preferably 5 to 15 wt. % water, particularly preferably 10 to less than 15 wt. % water. Such preferred compositions are referred to as "low-water."

As used herein, "anhydrous" means that a composition contains less than 5 wt. %, in particular less than 4 wt. %, preferably less than 3 wt. % water. Such anhydrous compositions are particularly preferred according to the invention.

The water content as defined herein relates the water content ascertained by means of Karl Fischer titration (Angewandte Chemie [applied chemistry] 1935, 48, 394-396; ISBN 3-540-12846-8 Eugen Scholz).

"Liquid" as used herein with reference to the washing agent according to the invention includes all compositions which are free-flowing at standard conditions (20° C., 1013 mbar) in the liquid phase and in particular also comprises gels and pasty compositions. In particular, the term also includes non-Newtonian liquids, which have a yield point.

All quantity specifications indicated in conjunction with the components described herein of the washing agent relate, if not otherwise indicated, to wt. %, each in relation to the total weight of the washing agent. Furthermore, such quantity specifications which relate to at least one component always relate to the total quantity of this type of component which is contained in the washing agent, if not explicitly indicated otherwise. This means that such quantity specifications, for example, in conjunction with "at least one non-ionic surfactant" relate to the total quantity of non-ionic surfactants which is contained in the washing agent.

"At least one" as used herein relates to 1 or more, for example, 1, 2, 3, 4, 5, 6, 7, 8, 9, or more. In conjunction with components of the compositions described herein, this specification does not relate to the absolute quantity of molecules but rather to the type of the components. "At least one non-ionic surfactant" therefore means, for example, one or more different non-ionic surfactants, i.e., one or more different types of non-ionic surfactants. Together with quantity specifications, the quantity specifications relate to the total quantity of the accordingly identified type of component, as already defined above. When reference is made herein to the pH value of the composition/the washing agent, the specified values always relate the pH value of a 1% (wt. %) solution of the washing agent in distilled water at 25° C.

The low-water to anhydrous liquid washing agent comprises 5 to 30 wt. %, preferably 10 to 30 wt. %, in particular 15 to 25 wt. % of at least one hydroxycarboxylic acid having 2 to 8 carbon atoms, wherein aliphatic hydroxycarboxylic acids having 2 to 8 carbon atoms are preferred.

The liquid washing agent according to the invention particularly preferably contains at least one hydroxycarboxylic acid selected from at least one representative of the group which is formed by citric acid, lactic acid, tartaric acid, hydroxysuccinic acid, and salicylic acid.

The liquid washing agent according to the invention very particularly preferably contains 5 to 30 wt. %, preferably 10 to 30 wt. %, in particular 15 to 25 wt. % of at least one aliphatic hydroxycarboxylic acid having 3 to 6 carbon atoms, wherein said hydroxycarboxylic acid is linear or branched.

The liquid washing agent according to the invention very particularly preferably contains 5 to 30 wt. %, preferably 10 to 30 wt. %, in particular 15 to 25 wt. % of at least one aliphatic hydroxycarboxylic acid having 3 to 6 carbon atoms selected from citric acid, lactic acid, or the mixture thereof.

Both anhydrous citric acid and also citric acid monohydrate or mixtures thereof can be used as citric acid. Citric acid monohydrate is preferably used.

Lactic acid is to be understood as both the racemate and also the optically active D/L variant.

In addition, mixtures of citric acid and lactic acid are well suitable, wherein while maintaining said total quantity of said hydroxy acids, the quantity of lactic acid is 1 to 10 wt. % and the quantity of citric acid is 4 to 29 wt. %.

If a combination of lactic acid and citric acid is used, it is preferable according to the invention to set the weight ratio of lactic acid to citric acid in a weight ratio range of 1 to 2 to 1 to 10, particularly preferably 1 to 3 to 1 to 7, very particularly preferably 1 to 4 to 1 to 6.

In this case, it is in turn most preferable to select, while maintaining said total quantity of said hydroxy acids, the quantity of lactic acid of 1 to 10 wt. % and the quantity of citric acid of 4 to 29 wt. % and to set the weight ratio of lactic acid to citric acid in a weight ratio range of 1 to 2 to 1 to 10, particularly preferably 1 to 3 to 1 to 7, very particularly preferably 1 to 4 to 1 to 6.

Furthermore, the liquid washing agent according to the present invention contains 5 to 55 wt. %, preferably 20 to 55 wt. %, in particular 35 to 50 wt. % of at least one non-ionic surfactant, in relation to the total quantity of the washing agent. Suitable non-ionic surfactants comprise all known surfactants which are typically used in washing agents, in particular those which are selected from the group consisting of alkyl glycol ethers, alkoxylated fatty alcohols, alkoxylated oxoalcohols, alkoxylated fatty acid alkyl esters, fatty acid amides, alkoxylated fatty acid amides, polyhydroxy fatty acid amides, alkyl phenol polyglycol ethers, amino oxides, alkyl (poly)glucosides, and mixtures thereof.

In various embodiments of the invention, the washing agents described herein comprise at least one fatty alcohol alkoxylate having the following formula (I)

$$R^1-O-(AO)_m-H \qquad (I),$$

wherein
$R^1$ is a linear or branched alkyl residue,
AO is an ethylene oxide (EO) or propylene oxide (PO) group,
m is an integer from 1 to 50.

In the above formula, R1 stands for a linear or branched, substituted or unsubstituted alkyl residue. In one preferred embodiment of the present invention, R1 is a linear or branched alkyl residue having 5 to 30 C atoms, preferably having 7 to 25 C atoms, and in particular having 10 to 19 C atoms. Preferred residues R1 are selected from decyl, undecyl, dodecyl, tridecyl, tetradecyl, pentadecyl, hexadecyl, heptadecyl, octadecyl, and nonadecyl residues and the mixtures thereof, wherein the representatives having even numbers of C atoms are preferred. Particularly preferred residues R1 are derived from fatty alcohols having 12 to 19 C atoms, for example, coconut fatty alcohol, tallow fatty alcohol, lauryl, myristyl, cetyl, or stearyl alcohol or from oxoalcohols having 10 to 19 C atoms.

AO is an ethylene oxide (EO) or propylene oxide (PO) group, preferably an ethylene oxide group. The index m is an integer from 1 to 50, preferably 2 to 20 and preferably 2 to 10. In particular, m is 3, 4, 5, 6, or 7. The agent according to the invention can contain mixtures of non-ionic surfactants which have various degrees of ethoxylation. Surfactants having degrees of alkoxylation/ethoxylation of at least 5 are preferred.

In summary, particularly preferred fatty alcohol alkoxylates are those of the formula

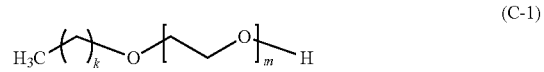

(C-1)

with k=9 to 17, m=3, 4, 5, 6, or 7. Very particularly preferred representatives are fatty alcohols having 10 to 18 C atoms and with 7 EO (k=11-17, m=7 in formula C-1).

Such fatty alcohol ethoxylates are available under the sales names Dehydol® LT7 (Cognis), Lutensol® AO7 (BASF), Lutensol® M7 (BASF), and Neodol® 45-7 (Shell Chemicals).

The above-mentioned fatty alcohol ethoxylates preferably have degrees of ethoxylation of at least 3, particularly preferably at least 5, in turn preferably 7. Such fatty alcohol ethoxylates can be used alone, as mixtures of such fatty alcohol ethoxylates, or also mixtures with lower ethoxylated fatty alcohol ethoxylates, for example, Lutensol® A03 (BASF). In such mixtures, it is preferable for the fatty alcohol ethoxylates having degrees of ethoxylation of at least 5, preferably 7, to make up at least 50 wt. %, preferably at least 75 wt. % of the total quantity of fatty alcohol ethoxylates.

Further usable non-ionic surfactants can be, for example:
polyol fatty acid esters, for example, the commercial product Hydagen® HSP (Cognis) or Sovermol types (Cognis),
alkoxylated triglycerides,
alkoxylated fatty acid alkyl esters of the formula $R^3CO-(OCH_2CHR^4)_wOR^5$, in which $R^3CO$ stands for a linear or branched, saturated and/or unsaturated acyl residue having 6 to 20 2C atoms, $R^4$ stands for hydrogen or methyl, and $R^5$ stands for linear or branched alkyl residues having 1 to 4 C atoms, and w is 1 to 20,
aminooxides,
hydroxy mixed ethers,
sorbitan fatty acid esters and addition products of ethylene oxide on sorbitan fatty acid esters, for example, polysorbates,
sugar fatty acid esters and addition products of ethylene oxide to sugar fatty acid esters,
addition products of ethylene oxide to fatty acid alkanol amides and fatty amines,
fatty acid-N-alkyl glucamides, and
alkyl(poly)glycosides of the formula $R^2O-[G]_p$,
in which $R^2$ is a linear or branched alkyl having 12 to 16 C atoms, G is a sugar residue with 5 or 6 C atoms, in particular glucose, and the index p is 1 to 10.

The at least one non-ionic surfactant which is used according to the invention preferably has an HLB value of at least 5 but at most 18, preferably of 8 to 17, and particularly preferably of 9 to 16.

The term "HLB" (hydrophilic-lipophilic balance) defines the hydrophilic and lipophilic component of corresponding substance classes (surfactants here) in a value range of 1 to 20 according to the following formula (Griffin, Classification of surface active agents by HLB, J. Soc. Cosmet. Chem. 1, 1949):

$$HLB = 20 \times (1 - (M_1/M))$$

with M=molar mass of the entire molecule
and Mi=molar mass of the lipophilic component of the molecule Low HLB values (≥1) describe lipophilic materials, high HLB values (≤20) describe hydrophilic materials. Thus, for example, defoamers typically have HLB values in the range of 1.5 to 3 and are insoluble in water. Emulsifiers for W/O emulsions typically have HLB values in the range of 3 to 8, while in contrast emulsifiers for O/W emulsions typically have HLB values in the range of 8 to 18. Cleansing substances typically have HLB values in the range of 13 to 15 and solubilizing agents have values in the range of 12 to 18.

In various embodiments of the invention, the non-ionic surfactants which are used according to the invention have critical micelle formation concentrations of 10-3 mol/L or more, in particular 10-2 mol/L for more. In accordance with the typical understanding in this field, the critical micelle formation concentration (CMC) indicates the surfactant concentration at which micelles form and all of the additional surfactant which is added travels into the micelles.

Furthermore, the washing agent can contain at least one anionic surfactant, in particular an alkyl benzene sulfonate and/or an alkyl either sulfate and/or a fatty acid soap. Such anionic surfactants can be used in the form of the salts thereof, or also as the corresponding acids.

In this case, preferably alkyl benzene sulfonates, olefin sulfonates, i.e., mixtures of alkene and hydroxy alkane sulfonates, and disulfonates, as are obtained, for example, from monoolefins having 12 to 18 C atoms with terminal or internal double bond by sulfonation with gaseous sulfur trioxide and subsequent alkaline or acid hydrolysis of the sulfonation products, come into consideration as surfactants of the sulfonate type. Alkane sulfonates having 12 to 18 C atoms and esters of α-sulfo fatty acids (ester sulfonates), for example, the α-sulfonated methyl esters of hydrogenated coconut, palm kernel, or tallow fatty acids.

Alkyl benzene sulfonates are preferably selected from linear or branched alkyl benzene sulfonates of the formula

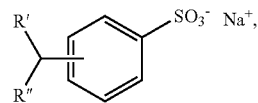

in which R' and R" are independently hydrogen or alkyl and together contain 9 to 19, preferably 9 to 15, and in particular 9 to 13 C atoms. A very particularly preferred representative is sodium dodecyl benzene sulfonate. The corresponding acids of the above-mentioned alkylbenzene sulfonates are used in various preferred embodiments.

The salts of the sulfuric acid semi esters of the fatty alcohols having 12 to 18 C atoms, for example, from coconut fatty alcohol, tallow fatty alcohol, lauryl, myristyl, cetyl, or stearyl alcohol or from oxoalcohols having 10 to 20 C atoms, and the semiesters of secondary alcohols of these chain lengths are preferred as alk(en)yl sulfates. The alkyl sulfates having 12 to 16 C atoms and alkyl sulfates having 12 to 15 C atoms and also alkyl sulfates having 14 and 15 C atoms are preferred from a washing aspect. Also, 2,3-alkyl sulfates are suitable anionic surfactants.

Alkyl ether sulfates with the formula

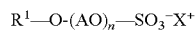

are also suitable. In this formula, $R^1$ stands for a linear or branched, substituted or unsubstituted alkyl residue, preferably for a linear, unsubstituted alkyl residue, particularly preferably for a fatty alcohol residue. Preferred residues $R^1$ are selected from decyl, undecyl, dodecyl, tridecyl, tetradecyl, pentadecyl, hexadecyl, heptadecyl, octadecyl, nonadecyl, and eicosyl residues and the mixtures thereof, wherein the representatives having an even number of C atoms are preferred. Particularly preferred residues $R^1$ are derived from fatty alcohols having 12 to 18 C atoms, for example, from coconut fatty alcohol, tallow fatty alcohol, lauryl, myristyl, cetyl, or stearyl alcohol or from oxoalcohols having 10 to 20 C atoms.

AO stands for an ethylene oxide (EO) or propylene oxide (PO) group, preferably for an ethylene oxide group. The index n is an integer from 1 to 50, preferably from 1 to 20, and in particular from 2 to 10. Very particularly preferably, n is 2, 3, 4, 5, 6, 7, or 8. X is a monovalent cation or the nth part of an n-valent cation, in this case the alkali metal ions are preferred, and among them Na+ or K+, wherein Na+ is extremely preferred. Further cations X+ can be selected from NH4+, ½Zn2+, ½Mg2+, ½Ca2+, ½Mn2+, and the mixtures thereof.

Particularly preferred washing agents contain an alkyl ether sulfate selected from fatty alcohol ether sulfates of the formula A-1

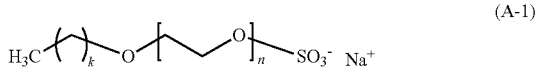

(A-1)

with k=11 to 19, n=2, 3, 4, 5, 6, 7, or 8. Very particularly preferred representatives are Na fatty alcohol ether sulfates with 12 to 18 C atoms and 2 EO (k=11 to 13, n=2 in formula A-1). The indicated degree of ethoxylation represents a statistical mean value, which can be an integer or a fraction for a special product. The indicated degrees of alkoxylation represent statistical mean values, which can be an integer or a fraction for a special product. Preferred alkoxylates/ethoxylates have a constricted homologous distribution (narrow range ethoxylates, NRE).

Furthermore, alkyl and/or alkenyl oligoglycoside carboxylates, sulfates, phosphates, and/or isethionates, which are derived from alkyl and/or alkenyl oligoglycosides of the general formula (A-2)

R⁶—O-(G)                                                         (A-2)

can be used, wherein
R⁶ alkyl with 6 to 22 C atoms or alkenyl with 6 to 22 C atoms,
G glycoside unit, which is derived from a sugar with 5 or 6 carbon atoms,
p number from 1 to 10.

The use of alkyl and/or alkenyl oligoglycoside carboxylates, sulfates, phosphates, and/or isethionates in textile treatment agents, for example, washing agents or fabric softeners, results, inter alia, in improved color stability of dyed textiles and improved cleaning power of the washing agent. Upon use in liquid agents, in particular liquid washing agents, the storage stability of the agent is increased in comparison to conventional color transfer inhibitors. Alkyl oligoglycoside carboxylates, sulfates, phosphates, and/or isethionates can be used, preferably alkyl oligoglycoside carboxylates or phosphates, in particular alkyl oligoglycoside carboxylates.

In the alkyl and/or alkenyl oligoglycosides, preferably in at least one of the residues G, at least one hydroxyl group is replaced by —O—C1-12-alkenyl-COOM, —OSO3M, —OP(O)(OM)2, or —O—CH2-CH2-SO3M, O—CH2-CH2-O—SO3M, each with M=H, alkali metal, or NH4. In this case, an alkyl oligoglycoside carboxylate is particularly preferably used, which accordingly contains —O—C1-12-alkylene-COOM or —O(CH2-)nCOOM with M=H, Na, or K and n=1 to 3. Particularly preferably, at least one OH group of the residue G is replaced according to the above formula by a group —O—CH2-COONa.

Particularly preferably, an alkyl oligoglycoside carboxylate is used, in which the alkyl residue is a lauryl residue. A lauryl glucoside carboxylate is especially preferred, as is available as Plantapon® LGC and Plantapon® LGC sorb from BASF SE.

In the alkyl glycosides of above formula (A-2), the glycoside units G are preferably derived from aldoses and/or ketones.

The saccharides having a reducing effect, the aldoses, are preferably used because of the better reactivity. The glucoses in particular come into consideration among the aldoses because of the easy accessibility and technical availability thereof. The alkyl glycosides which are particularly preferably used as starting materials are therefore the alkyl glucosides.

The index number p indicates the degree of oligomerization, i.e., the distribution of monoglycosides and oligoglycosides, and stands for a number between 1 and 10. While p in a given compound always has to be an integer and can assume above all the values p=1 to 6 here, the value p for a certain alkyl glycoside is an analytically determined computed variable, which usually represents a fraction. Alkyl glycosides having a mean degree of oligomerization p of 1.1 to 3.0 are preferably used. Those alkyl glycosides, the degree of oligomerization of which is less than 1.5 and in particular is between 1.1 and 1.4, are particularly preferred.

The alkyl residue R is primarily derived from primary alcohols having 6 to 22, preferably 12 to 18 C atoms. Typical examples are capron alcohol, capryl alcohol, caprin alcohol, lauryl alcohol, myristyl alcohol, cetyl alcohol, stearyl alcohol, and behenyl alcohol, and also industrial fractions which, in addition to the mentioned saturated alcohols, can also contain components of unsaturated alcohols and are obtained on the basis of natural fats and oils, for example, palm oil, palm kernel oil, coconut oil, or beef tallow. The use of industrial coconut alcohol is particularly preferable in this case.

In addition to the mentioned fatty alcohols, the alkyl glycosides can also be derived from synthetic primary alcohols having 6 to 22 C atoms, in particular the so-called oxoalcohols, which can have a component of 5 to 40 wt. % branched isomers.

Particularly preferred alkyl residues are those having 8/10, 12/14, 8 to 16, 12 to 16, or 16 to 18 C atoms. Mixtures of the alkyl residues result in the case of production proceeding from natural fats and oils or mineral oils.

Methods for producing these alkyl glycosides are described, for example, in American patent specifications U.S. Pat. No. 3,547,828 and U.S. Pat. No. 3,839,318 and German patent application DE 3723826. For alkyl polyglycosides per se, reference can be made, for example, to DE 10027975, DE 10138094, and DE 10031014.

For a further discussion of alkyloligo/polyglycosides (APG), reference is made to international patent publication WO 03013450.

The production of the alkyl and/or alkenyl oligoglycoside carboxylates, phosphates, sulfates, and/or isethionates used according to the invention can be performed according to known methods. The production of the carboxylates is performed, for example, by reacting the alkyloligoglycosides with salts of chlorine carboxylic acids in the presence of basis. For example, a reaction can be performed using 2-chlorine acetic acid sodium salt in the presence of NaOH. During the reaction, both the hydroxyl groups in the ring and also the —CH2-OH group can be reacted. The degree of reaction is dependent, inter alia, on the stoichiometry of the feedstocks. The alkyloligoglycosides are preferably at least reacted on the —CH2-OH-group, wherein optionally an average of one or more of the hydroxyl groups located on the ring can be reacted.

Further hydroxyl groups can also be etherified, for example.

The production of the isethionates is described, for example, in WO 9426857. The production of the sulfates is described, for example, in WO 9310208 and WO 9115192. In the latter document, mixtures of the APG sulfates with, inter alia, alkyl sulfates or alkyl ether sulfates and further ingredients are also described. The production of the sulfates can additionally be performed as described in EP 0186242. For example, the corresponding alkyl glycoside can be reacted with gaseous sulfur trioxide or with sulfuric acid, followed by neutralization.

The anionic surfactants including the fatty acid soaps can be provided in the form of the sodium, potassium, or magnesium or ammonium salts thereof. The anionic surfactants are preferably provided in the form of the sodium salts and/or ammonium salts thereof. Amines usable for neutralization are preferably choline, triethylamine, monoethanolamine, diethanolamine, triethanolamine, methylethylamine, or a mixture thereof, wherein monoethanolamine is preferred. As already described above, however, the anionic surfactants can also be used as the acid.

As a further required component, the liquid washing agent according to the invention contains at least one α-amylase with a pH optimum of <pH 7. It is preferable in this case if the liquid washing agent according to the invention contains at least one α-amylase with a pH optimum in the pH range from pH 1 to pH 6. The pH optimum of the α-amylase according to the invention is determined according to Chang et al., as described in Biochemistry and Molecular Biology International, Volume 36, No. 1, May 1995, 185-193. Reference is made to this document expressly and in its entirety.

Such α-amylases according to the invention are produced and secreted by microorganisms, i.e., fungi or bacteria, above all those of the genera *Aspergillus* and *Bacillus*. Proceeding from these natural enzymes, furthermore a nearly unmanageable abundance of variants is available, which have been derived via mutagenesis and which have specific advantages depending on the field of use Preferred α-amylases according to the invention are selected from at least one α-amylase from *Aspergillus oryzae*, from *Penicillium oxalicum*, from *Micrococcus* sp. NS 211, from *Bacillus* sp. *Ferdowsicous*.

The washing agents described herein are preferably homogeneous, low-viscosity solutions of citric acid in the remaining components of the washing agent, i.e., essentially the surfactants used. "Homogeneous" as used in this context relates to molecularly-dispersed solutions and colloid solutions which are stable under standard conditions, i.e., after 24 hours at room temperature (25° C.) and 1013 mbar, have no visually perceptible phase separation, including precipitation.

"Low viscosity" as used herein means that the low-water to anhydrous liquid washing agent as described herein has a viscosity less than 15,000 mPas, preferably of 1,000 to 5,000 mPas, still more preferably of 2,000 to 3,000 mPas (Brookfield viscosimeter, spindle number 3 at 20° C.).

The liquid washing agents additionally contain, in preferred embodiments, one or more nonaqueous, organic solvents. It is preferable in this case for the washing agent to contain greater than 1 wt. %, preferably greater than 5 wt. %, and particularly preferably greater than 10 wt. %, each in relation to the total quantity of washing agent, of nonaqueous solvent. Particularly preferred liquid washing agents contain—in relation to the weight thereof—1 to 80 wt. %, preferably 1 to 65 wt. %, preferably 1 to 50 wt. %, particularly preferably 5 to 40 wt. %, and in particular 10 to 30 wt. % nonaqueous solvent.

Suitable nonaqueous solvents comprise monovalent or multivalent alcohols, alkanol amines, or glycol ethers. The solvents are preferably selected from ethanol, n-propanol, i-propanol, butanolene, glycol, propane diol, butane diol, methylpropane diol, glycerin, glycols, such as diglycol, propyl diglycol, butyl diglycol, hexylene glycol, ethylene glycol methyl ether, ethylene glycol ethyl ether, ethylene glycol propyl ether, ethylene glycol mono-n-butyl ether, diethylene glycol methyl ether, diethylene glycol ethyl ether, propylene glycol methyl ether, propylene glycol ethyl ether, propylene glycol propyl ether, dipropylene glycol monomethyl ether, dipropylene glycol monoethyl ether, methoxytriglycol, ethoxytriglycol, butoxytriglycol, 1-butoxyethoxy-2-propanol, 3-methyl-3-methoxybutanol, 2,2-dimethyl-4-hydroxymethyl-1,3-dioxolane, propylene-glycol-t-butyl ether, di-n-octyl ether, and low-molecular-weight polyalkylene glycols, such as PEG 400, and also mixtures of the solvents. In one preferred embodiment, the nonaqueous solvent is selected from the group consisting of ethanol, n-propanol, i-propanol, butanolene, glycol, propane diol, butane diol, methyl propane diol, glycerin or mixtures thereof. In one preferred embodiment, the nonaqueous solvent is 1,2-propane diol, glycerin, or a mixture thereof, very particularly preferably glycerin.

In general, the pH value of the liquid washing agent according to the invention can be set by means of typical pH regulators. However, the pH value is typically in the desired range due to the use of hydroxycarboxylic acid having 2 to 8 carbon atoms in the indicated quantities.

Suitable further pH adjusting agents include acids and/or bases. Suitable acids are, in addition to said low-molecular-weight hydroxycarboxylic acids, further organic acids such as acetic acid, succinic acid, adipic acid, or also amidosulfonic acid and mixtures thereof. In addition, however, the mineral acids hydrochloric acid, sulfuric acid, and nitric acid and/or the mixtures thereof can also be used. Suitable bases originate from the group of alkaline and alkaline earth metal hydroxides and carbonates, in particular alkali metal hydroxides, of which potassium hydroxide and above all sodium hydroxide is preferred. Volatile bases can also be used, for example, in the form of ammonia and/or alkanolamines, which can contain up to 9 C atoms in the molecule. The alkanolamine is preferably selected in this case from the group consisting of mono-, di-, triethanolamine and propanolamine and the mixtures thereof.

In addition, the washing agent can contain further ingredients which further improve the application-technology and/or aesthetic properties of the washing agent. In the scope of the present invention, the washing agent preferably additionally contains one or more materials from the group of structural materials/complex formers, bleaching agents, electrolytes, perfumes, perfume carriers, fluorescence agents, colorants, hydrotropes, foam inhibitors, silicone oils, antiredeposition agents, graying inhibitors, shrinkage prevention agents, wrinkle protection agents, color transfer inhibitors, antimicrobial active ingredients, germicides, fungicides, antioxidants, preservatives, corrosion inhibitors, antistatic agents, bittering agents, ironing aids, repellent and impregnation agents, swelling and anti-slip agents, softener components, and UV absorbers.

If the washing agent according to the invention contains bleaching agent, hydrogen peroxide and/or PAP (phthalimido peroxyhexanoic acid) is preferably used as the bleaching agent.

In particular polymers based on terephthalate-PEG, as are commercially available under the tradename Texcare®, are usable as antiredeposition agents. Alternatively, (co-)polymers based on polyethylene imine, polyvinylacetate, and polyethylene glycol are also usable, preferably in mixtures with antiredeposition agents.

In particular, organic structural materials are suitable as additional structural materials, for example, the polycarboxylic acids usable in the form of the sodium salts thereof or also as acids, wherein polycarboxylic acids are understood as those carboxylic acids which carry more than one acid function. For example, these are adipic acid, glutaric acid, maleic acid, fumaric acid, amino carboxylic acids, in particular glutamic acid-N,N-diacetic acid (GLDA) and methyl glycine-N,N-diacetic acid (MGDA), and mixtures thereof. Further polymer polycarboxylates are suitable as structural materials. These are, for example, the alkali metal salts of polyacrylic acid or polymethacrylic acid, for example, those having a relative molecular mass of 600 to 750,000 g/mol. Suitable polymers are in particular polyacrylates, which preferably have a molecular mass of 1,000 to 15,000 g/mol. Because of the superior solubility thereof, in turn the short-chain polyacrylates, which have molar masses of 1,000 to 10,000 g/mol, and particularly preferably 1,000 to 5,000 g/mol, are preferred from this group. Furthermore, co-polymeric polycarboxylates, in particular those of acrylic acid with methacrylic acid and acrylic acid or methacrylic acid with maleic acid, are suitable. To improve the water solubility, the polymers can also contain allyl sulfonic acids, such as allyl oxybenzene sulfonic acid and methallyl sulfonic acid, as monomers. Soluble structural materials, such as acrylic polymers having a molar mass of 1,000 to 5,000 g/mol, are preferably used in liquid washing agents.

In various embodiments of the invention, the liquid washing agent can furthermore contain oxalic acid in quantities, in relation to the total weight of the liquid washing agent, of up to 15 wt. %, in particular 1-12 wt. %. The oxalic acid can further increase the effectiveness of the washing agent in the removal of rust spots.

The washing agents described herein can be produced by means of methods known in the prior art. In one aspect, the invention also relates to methods for producing the washing agents described herein. Such methods can comprise the following steps, for example:

1) producing a homogeneous solution of the hydroxycarboxylic acid with 2 to 8 carbon atoms in the at least one non-ionic surfactant or a mixture of the at least one non-ionic surfactant and additionally optionally the non-aqueous, organic solvents; and
2) adding the α-amylase used according to the invention and the optional remaining components of the washing agent.

For this purpose, the production can be performed in any arbitrary sequence of steps 1) and 2).

The washing agents described herein can be decanted into a water-soluble envelope and can therefore be a component of a water-soluble portion. If the washing agent is packaged in a water-soluble envelope, it is preferable for the content of water to be less than 10 wt. %, in relation to the total washing agent, and for anionic surfactants, if present, to be provided in the form of the ammonium salts thereof or as free acids.

The neutralization using amines does not result in the formation of water, in contrast to bases such as NaOH or KOH. Therefore, low-water washing agents can be produced, which are suitable directly for use in water-soluble envelopes. The water component can be reduced by suitable salts, for example, $MgSO_4$, $MgCO_3$, $Na_2SO_4$, $Na_2CO_3$, and mixtures thereof.

A water-soluble portion contains, in addition to the washing agent, a water-soluble envelope. The water-soluble envelope is preferably formed by a water-soluble film material.

Such water-soluble portions can be produced either by methods of vertical form fill seal (VFFS) or hot forming methods.

The hot forming method generally includes the forming of a first layer from a water-soluble film material to form bulges to accommodate a composition therein, decanting the composition into the bulges, covering the bulges filled with the composition with a second layer of a water-soluble film material, and sealing the first and second layers to one another at least around the bulges.

The water-soluble envelope is preferably formed from a water-soluble film material selected from the group consisting of polymers or polymer mixtures. The envelope can be formed from one or from two or more layers of the water-soluble film material. The water-soluble film material of the first layer and the further layers, if present, can be identical or different.

The water-soluble portion, comprising the washing agent and the water-soluble envelope, can have one or more chambers. The liquid washing agent can be contained in one or more chambers, if present, of the water-soluble envelope. The quantity of liquid washing agent preferably corresponds to the full or half dose which is required for a washing cycle.

It is preferable for the water-soluble envelope to contain polyvinyl alcohol or a polyvinyl alcohol copolymer.

Suitable water-soluble films for producing the water-soluble envelope are preferably based on a polyvinyl alcohol or a polyvinyl alcohol copolymer, the molecular weight of which is in the range of 10,000 to 1,000,000 g/mol, preferably 20,000 to 500,000 g/mol, particularly preferably 30,000 to 100,000 g/mol, and in particular 40,000 to 80,000 g/mol.

In addition, polymers selected from the group comprising polymers containing acrylic acid, polyacrylamides, oxazoline polymers, polystyrene sulfonates, polyurethanes, polyesters, polyether polylactic acid, and/or mixtures of the above polymers can be added to a film material suitable for producing the water-soluble envelope.

Preferred polyvinyl alcohol copolymers comprise, in addition to vinyl alcohol, dicarboxylic acids as further monomers. Suitable dicarboxylic acids are itaconic acid, malonic acid, succinic acid, and mixtures thereof, wherein itaconic acid is preferred.

Preferred polyvinyl alcohol copolymers also comprise, in addition to vinyl alcohol, an ethylene unsaturated carboxylic acid, or the salt or ester thereof. Particularly preferably, such polyvinyl alcohol copolymers contain, in addition to vinyl alcohol, acrylic acid, methacrylic acid, acrylic acid ester, methacrylic acid ester, or mixtures thereof.

Suitable water-soluble films for use in the envelopes of the water-soluble portions are films which are sold by MonoSol LLC, for example, under the designation M8630, C8400, or M8900. Other suitable films comprise films having the designation Solublon® PT, Solublon® GA, Solublon® KC, or Solublon® KL from Aicello Chemical Europe GmbH or the films VF-HP from Kuraray.

The water-soluble packages can have a substantially dimensionally stable spherical and cushion-shaped embodiment having a circular, elliptical, square, or rectangular basic shape.

The water-soluble package can have one or more chambers for storing one or more agents. If the water-soluble portion has two or more chambers, at least one chamber contains a liquid washing agent. The further chambers can each contain a solid or a liquid washing agent.

All substantive matters, subject matters, and embodiments which are described for the washing agents are also applicable to the use and the washing method and vice versa.

In a further aspect, the present invention is directed to the use of a liquid washing agent as described herein for washing textiles, in particular for removing stains which are based on components and residues of deodorants.

In a further aspect, the present invention is directed to a washing method, wherein a liquid washing agent as described herein is used. In this case, as already mentioned, the stain can be pre-treated using the liquid washing agent according to the invention before the actual washing method and/or firstly a washing solution can be provided, which contains the liquid washing agent according to the invention and which is subsequently brought into contact with the textile to be cleaned.

Methods for cleaning textiles are generally distinguished in that, in multiple method steps, various cleansing substances are applied to the material to be cleaned and are washed off after the action time, or the material to be cleaned is treated in another manner using a washing agent or a solution of this agent.

In the described washing methods, in various embodiments of the invention, temperatures of 60° C. or less, for example, 40° C. or less are used. These temperature specifications relate to the temperatures used in the washing steps.

All embodiments described herein in conjunction with the washing agents of the invention, in particular with regard to the specification of the ingredients, are applicable similarly to the described methods and uses and vice versa.

In preferred embodiments of the invention, the liquid washing agents contain, in relation to the total weight thereof, 10 to 25 wt. % hydroxycarboxylic acid selected from citric acid, lactic acid, or the mixture thereof, 40 to 50 wt. % of at least one non-ionic surfactant, preferably a fatty alcohol ethoxylate having 5 to 7 EO, more preferably a C13 to 15 fatty alcohol having 7 EO, for example, Lutensol® AO7, 1 to 15 wt. % water, 15 to 25 wt. % glycerin or 1,2-propane diol, preferably glycerin and at least one α-amylase having a pH optimum of pH <7, in particular pH 1 to 6. In addition, 5 to 8 wt. % fatty acid, in particular C12 to 18 fatty acid and/or 4 to 5 wt. % fragrances/fragrance composition and/or 6 to 9 wt. % antiredeposition agent, for example, Texcare® SRN-170 (70%) can preferably be included.

In preferred embodiments of the invention, the liquid washing agents contain, in relation to the total weight thereof, 10 to 25 wt. % hydroxycarboxylic acid selected from citric acid, lactic acid, or the mixture thereof, 40 to 50 wt. % of at least one non-ionic surfactant, preferably a fatty alcohol ethoxylate having 5 to 7 EO, more preferably a C13 to 15 fatty alcohol having 7 EO, for example, Lutensol® AO7, 1 to 15 wt. % water, 15 to 25 wt. % glycerin or 1,2-propane diol, preferably glycerin, at least one α-amylase having a pH optimum of pH <7, in particular pH 1 to 6, and at least one protease having a pH optimum of pH <7, in particular pH 1 to 6. In addition, 5 to 8 wt. % fatty acid, in particular C12 to 18 fatty acid and/or 4 to 5 wt. % fragrances/fragrance composition and/or 6 to 9 wt. % antiredeposition agent, for example, Texcare® SRN-170 (70%) can preferably be included.

Examples

|  | E1 |
|---|---|
| $C_{13-15}$ oxoalcohol having 7 units ethylene oxide (non-ionic surfactant) | 43.5 |
| $C_{12-18}$ coconut fatty acid | 6.2 |
| glycerin | 18.7 |
| Citric acid*1H2O | 18.7 |
| Perfume | 4.0 |
| Ester of propane diol, phthalic acid, and alphamethyl-omega-hydroxypoly(oxy-1,2-ethane diyl) (CAS 139755-78-5) | 8.1 |
| α-amylase from *Aspergillus Oryzae* having a pH optimum of pH 5.5 | 0.8 |
| pH value of a 1 wt.% solution in distilled water at 25° C. | 4.6 |
| Viscosity measurement [mPas] | 2900 |
| Visual appearance | clear |

The above specifications of the components are specified in wt. %. The formulations were dissolved in 1 L water and studied for the appearance thereof. The viscosity measurements were carried out using a Brookfield viscosity meter, spindle number 3 at 20° C.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A liquid washing agent, comprising, in relation to the total weight of the liquid washing agent,
    (i) 5 to 30 wt. % of at least one hydroxycarboxylic acid having 2 to 8 carbon atoms and
    (ii) 15 to 55 wt. % of at least one non-ionic surfactant,
    (iii) 0 to 20 wt. % water,
    (iv) at least one α-amylase having a pH optimum of pH <7,
    (v) greater than 10 wt. % nonaqueous solvent,
    wherein the liquid washing agent has a pH value <6.5.

2. The liquid washing agent according to claim 1, wherein at least one aliphatic hydroxycarboxylic acid having 3 to 6 carbon atoms is included as said hydroxycarboxylic acid, and wherein said hydroxycarboxylic acid is linear or branched.

3. The liquid washing agent according to claim 1, wherein at least one hydroxycarboxylic acid selected from the group consisting of citric acid, lactic acid, tartaric acid, hydroxysuccinic acid, and salicylic acid.

4. The liquid washing agent according to claim 1, wherein the at least one non-ionic surfactant comprises a fatty alcohol ethoxylate.

5. The liquid washing agent according to claim 1, wherein the agent comprises at least one α-amylase having a pH optimum of pH 1 to pH 6.

6. The liquid washing agent according to claim 1, wherein said α-amylase is selected from at least one α-amylase: from *Aspergillus oryzae*, from *Penicillium oxalicum*, from *Micrococcus* sp. NS 211, from *Bacillus* sp. *Ferdowsicous*.

7. The liquid washing agent according to claim 1, wherein the liquid washing agent is homogeneous and/or has a viscosity less than 15,000 mPas.

8. The liquid washing agent according to claim 1, wherein the agent furthermore contains at least one component selected from the group consisting of further surfactants, further enzymes, structural materials, bleaching agents, electrolytes, perfumes, perfume carriers, fluorescence agents, colorants, hydrotropes, foam inhibitors, silicone oils, antiredeposition agents, graying inhibitors, shrinkage prevention agents, wrinkle protection agents, color transfer inhibitors, antimicrobial active ingredients, germicides, fungicides, antioxidants, preservatives, corrosion inhibitors, antistatic agents, bittering agents, ironing aids, repellent and impregnation agents, swelling and anti-slip agents, softener components, and UV absorbers.

9. The liquid washing agent according to claim 1, wherein the agent is located in a water-insoluble, water-soluble, or water-dispersible package.

10. A washing method for washing textiles, wherein a washing agent according to claim 1 is contacted with textiles in a wash liquor.

* * * * *